United States Patent [19]
Buchanan et al.

[11] Patent Number: 5,443,434
[45] Date of Patent: Aug. 22, 1995

[54] EXERCISE DEVICE

[75] Inventors: Matthew D. Buchanan, Olney; Jeffrey D. Metcalf, Albion; Craig A. Topp, Olney, all of Ill.

[73] Assignee: Roadmaster Corporation, Olney, Ill.

[21] Appl. No.: 117,581

[22] Filed: Sep. 7, 1993

Related U.S. Application Data

[63] Continuation-in-part of Ser. No. 9,633, Jun. 17, 1993, Pat. No. Des. 353,638.

[51] Int. Cl.6 ............................................. A63B 21/00
[52] U.S. Cl. ..................................... 482/59; 482/111
[58] Field of Search ....................... 482/57, 59, 58, 63, 482/111–112; 428/318.6

[56] References Cited

U.S. PATENT DOCUMENTS

| | | | |
|---|---|---|---|
| D. 298,267 | 10/1988 | Nakao et al. | |
| D. 305,677 | 1/1990 | Beistegui | |
| D. 307,167 | 4/1990 | Lucas et al. | |
| D. 318,505 | 7/1991 | Gustafsson et al. | |
| D. 319,480 | 8/1991 | Byrd et al. | |
| D. 319,675 | 9/1991 | Byrd et al. | |
| D. 325,946 | 5/1992 | Cesaroni et al. | D21/194 |
| 4,082,264 | 4/1978 | Santos | 482/112 |
| 4,244,021 | 1/1981 | Chiles, III | |
| 4,509,742 | 4/1985 | Cones | |
| 4,558,861 | 12/1985 | Gall | |
| 4,589,656 | 5/1986 | Baldwin | 482/59 |
| 4,666,768 | 5/1987 | Tschudin-Mahrer | 428/318.6 |
| 4,786,049 | 11/1988 | Lautenschlager | |
| 4,824,102 | 4/1989 | Lo | |
| 4,850,587 | 7/1989 | Lin | |
| 4,852,872 | 8/1989 | Lo | 482/59 |
| 4,880,225 | 11/1989 | Lucas et al. | |
| 4,917,376 | 4/1990 | Lo | 482/62 |
| 4,932,649 | 6/1990 | Chen | |
| 4,932,650 | 6/1990 | Bingham et al. | 482/59 |
| 4,961,569 | 10/1990 | Roberge | |
| 4,981,294 | 1/1991 | Dalebout et al. | |
| 5,016,870 | 5/1991 | Bulloch et al. | |
| 5,031,900 | 7/1991 | Leask | |
| 5,149,312 | 9/1992 | Croft et al. | |

*Primary Examiner*—Stephen R. Crow
*Attorney, Agent, or Firm*—Steven P. Shurtz; Willian Brinks Hofer Gilson & Lione

[57] ABSTRACT

A quiet air resistance exercise cycle has a number of sound reduction features in its preferred embodiments. Soundproofing material is used on the inside of the housing surrounding the wheel to absorb sound. The housing comprises solid panels to limit air from outside the housing from contacting the wheel. The housing panels generally defining a polyhedron to create dead spaces for air eddies inside the wheel compartment. The wheel may also include a pitch reduction material and preferably is belt driven.

15 Claims, 8 Drawing Sheets

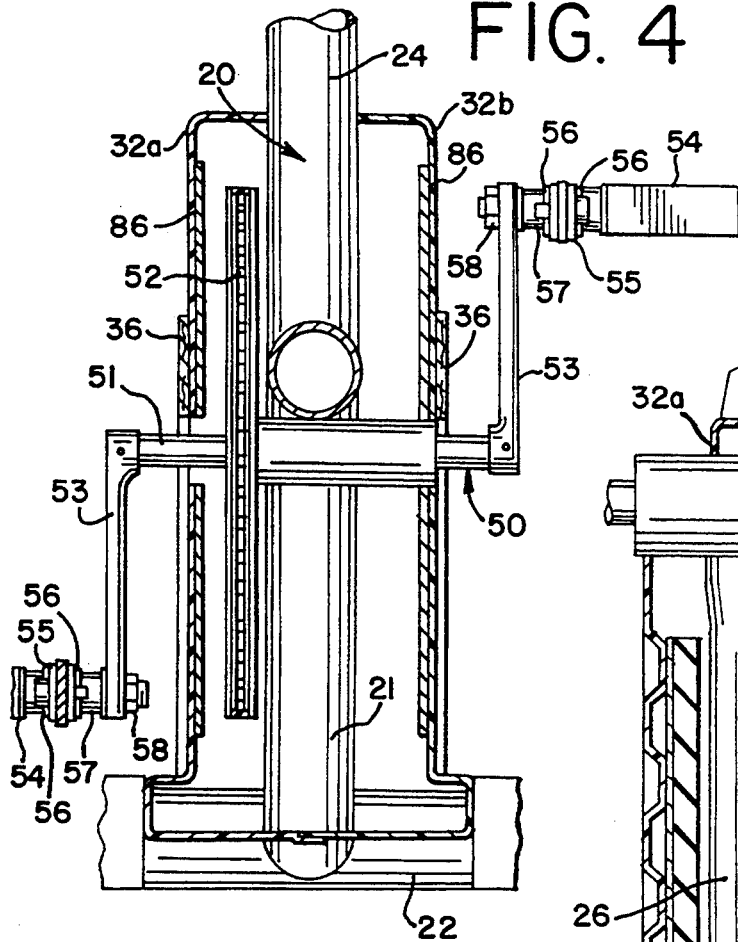
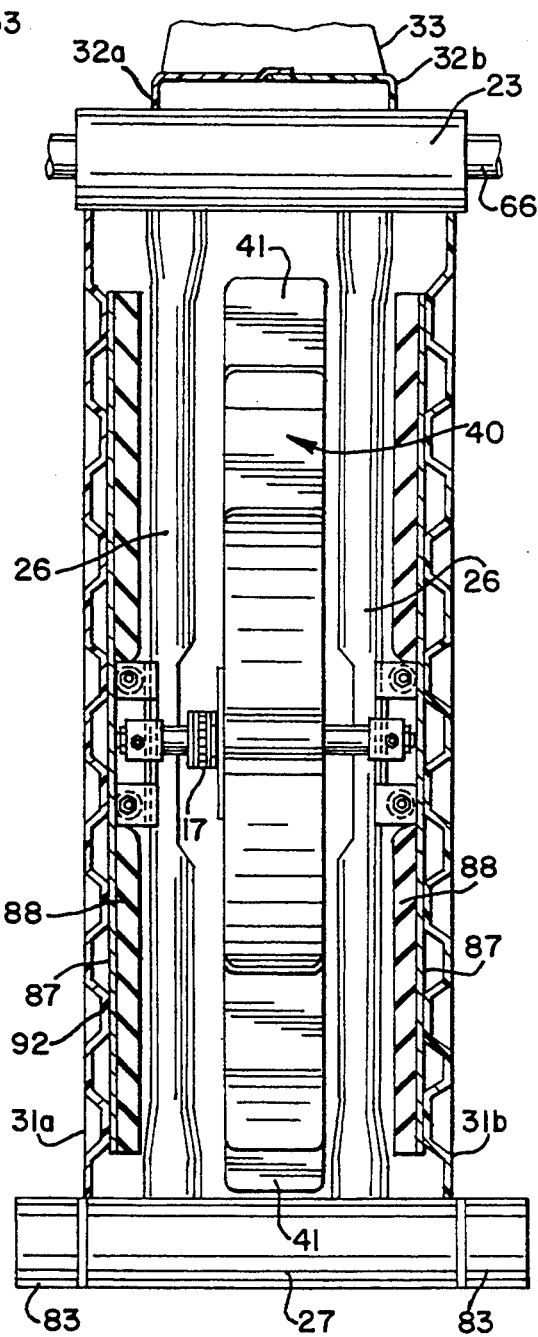

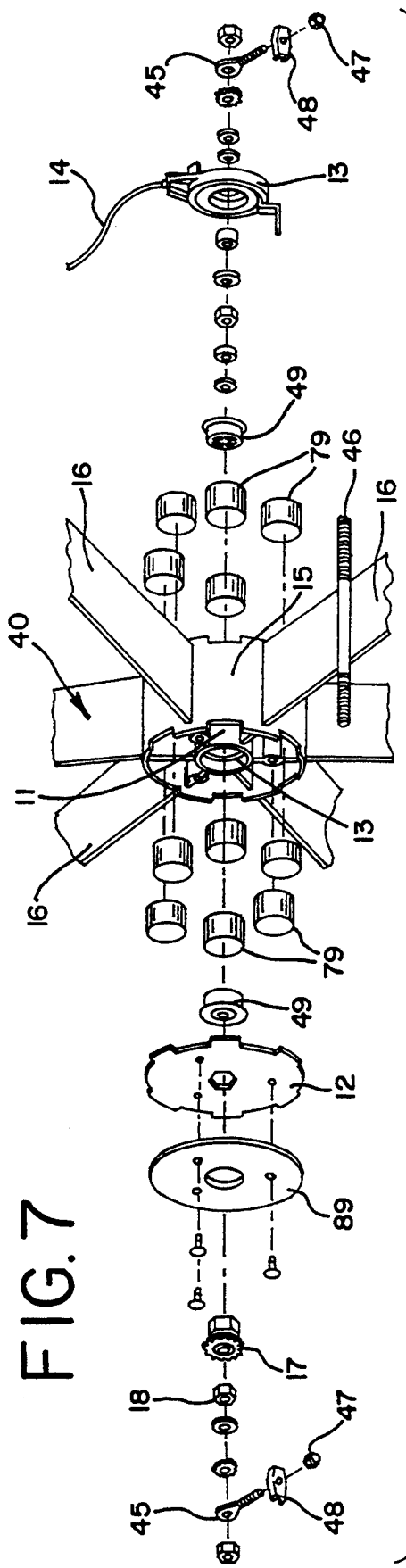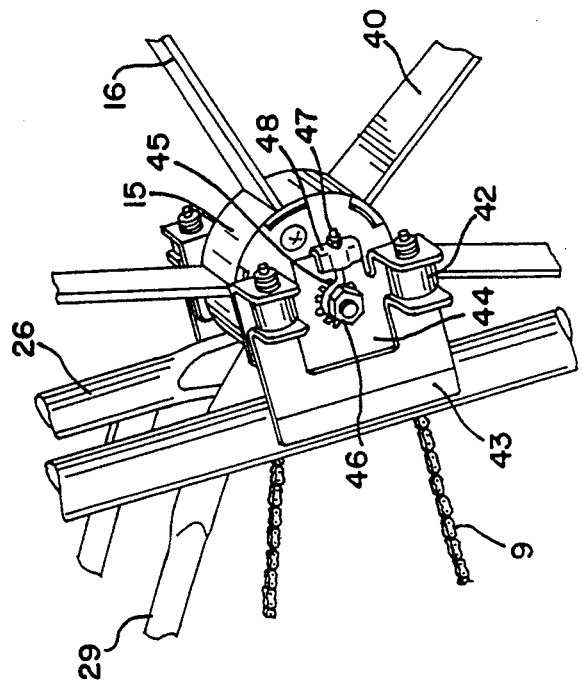

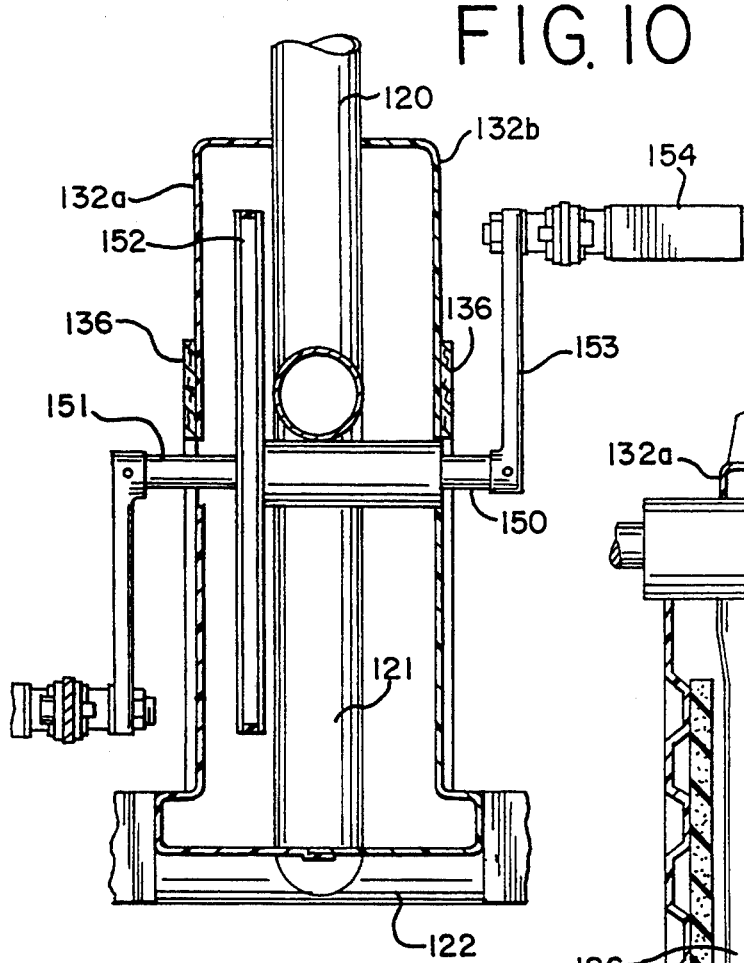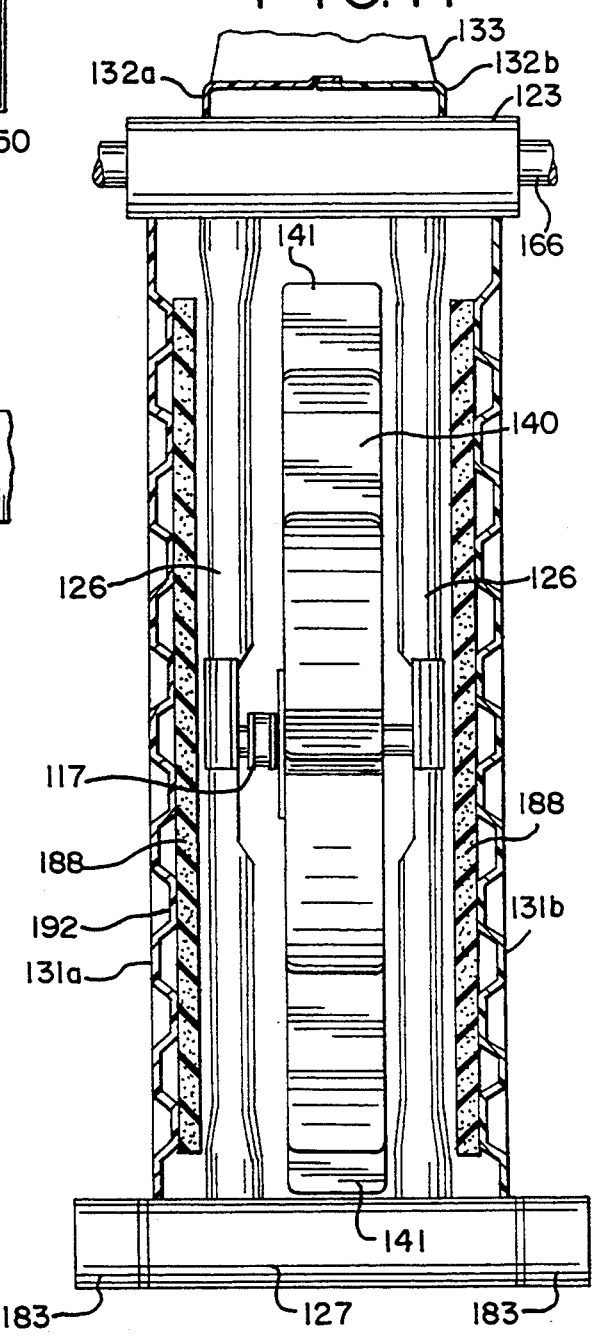

EXERCISE DEVICE

CROSS REFERENCE TO RELATED APPLICATIONS

The present application is a continuation-in-part of application Ser. No. 29/009,633 filed Jun. 17, 1993 now Design Pat. No. D353638.

BACKGROUND OF THE INVENTION

This invention relates to exercise equipment, and in particular, to an exercise cycle.

Exercise cycles benefit the user by improving cardiovascular fitness, enhancing body tone and engendering an overall sense of well being. Exercise cycles often include only one wheel mounted for rotation on a stand. The wheel often has vanes or paddles which increase the resistance to air and thus enhance the user's workout. Typically, to increase the wheel's air resistance, the user pedals faster. Other exercise cycles rely on friction straps or electromagnetic sources of resistance.

One complaint often made about the use of exercise cycles, particularly air resistance exercise cycles, is the noise generated by operation of the device. The noise at a user's ear level for a typical air resistance exercise cycle is believed to be in the range of 65-70 decibels. In an air resistance exercise cycle, the blades moving the air inherently generate sound. To allow the air to move and contact the blades on the wheel, air resistance exercise cycles typically use a shroud surrounding the wheel having panels with vents in it. Unfortunately, the sound from the mechanical portions of the device are therefore also able to emanate from the device, increasing the noise. Thus there has been a long felt need for a quiet air resistance exercise cycle.

SUMMARY OF THE INVENTION

A quiet exercise device has been invented that overcomes the problems noted above in several unique ways.

In one aspect, the invention is an exercise device comprising a frame, pedals attached to a crank rotatably mounted to the frame, and soundproofing material supported by the frame to absorb sound generated by operation of the exercise cycle when the crank is rotated.

In another aspect, the invention is an air resistance exercise cycle comprising a frame, pedals attached to a crank rotatably mounted to the frame, a wheel comprising air resistance blades rotatably supported by the frame and connected to the crank so as to be driven by rotation of the crank, and a housing, comprising solid panels, so as to limit air from outside the housing from contacting the wheel.

In a third aspect, the invention is an air resistance exercise cycle comprising a frame, pedals attached to a crank rotatably mounted to the frame, a wheel comprising air resistance blades rotatably supported by the frame and connected to the crank so as to be driven by rotation of the crank, and a housing surrounding the wheel, the housing comprising two solid side wall panels generally perpendicular to the axis of rotation of the wheel and edge panels extending between the side wall panels, the side wall and edge panels generally defining a polyhedron.

In a fourth aspect, the invention is an exercise cycle comprising a frame, pedals attached to a crank rotatably mounted to the frame, and a wheel rotatably supported by the frame and connected to the crank so as to be driven by rotation of the crank, the wheel further comprising a pitch reduction material that lowers the pitch of sound emanating from the wheel when it is rotated.

The use of soundproofing material, particularly foam on the inside of the housing covering the wheel, reduces noise emanating from the device. By using solid panels in the housing to surround the wheel, sound from inside the housing is prevented from directly traveling outside the device. It has been found that the use of a generally polyhedron shape for the housing surrounding the wheel allows for air resistance even though the housing comprises solid panels, because the air eddies inside the housing. It was also discovered that reducing the pitch of the sound generated by the exercise device significantly reduced the perceived noise of the device.

These features have made it possible to have a quiet air resistance exercise cycle, one that produces less than 60 decibels measured at the ear level of a rider when pedaled at 50 rpm. These and other advantages of the invention, as well as the invention itself, will be more easily understood in view of the attached drawings, a brief description of which follows.

BRIEF DESCRIPTION OF THE DRAWINGS

FIG. 4 is a cross-sectional view taken on line 4—4 of FIG. 3.

FIG. 5 is a cross-sectional view taken on line 5—5 of FIG. 3.

FIG. 7 is an exploded view of the wheel hub assembly of the exercise cycle of FIG. 1.

FIG. 8 is a perspective view of the wheel mounting system of the exercise cycle of FIG. 1.

FIG. 10 is a cross-sectional view taken along line 10—10 of FIG. 9.

FIG. 11 is a cross-sectional view taken along line 11—11 of FIG. 9.

DETAILED DESCRIPTION OF THE DRAWINGS AND PREFERRED EMBODIMENTS OF THE INVENTION

Figure 1:
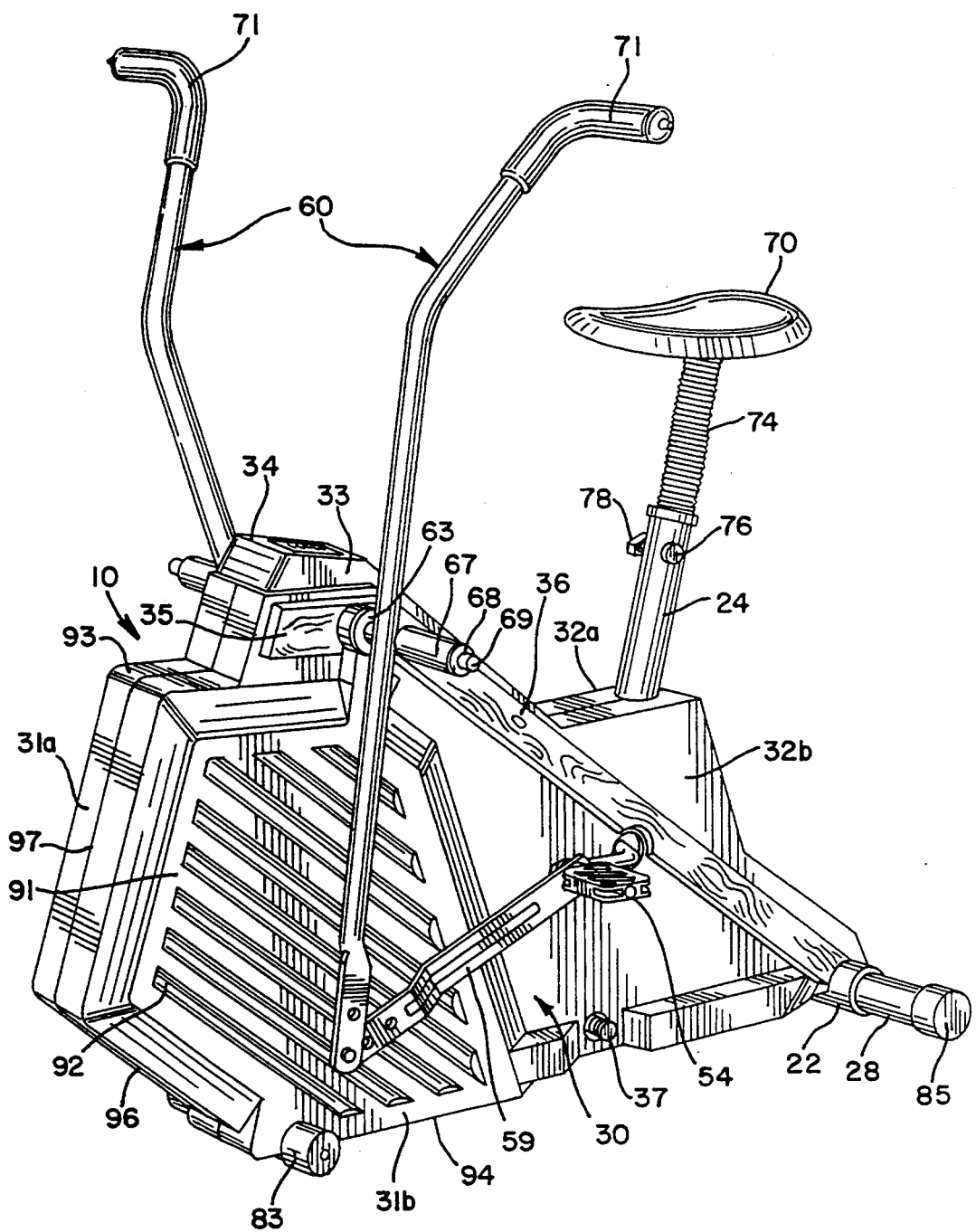
FIG. 1 is a perspective view of an exercise cycle of the present invention.

A first preferred embodiment of the invention is shown in FIGS. 1-8. As shown generally in FIGS. 1-3 and 6, the air resistance exercise cycle 10 comprises a frame 20, a housing 30, a wheel 40, a crank assembly 50, handlebars 60 and a seat 70. As explained more fully below, the exercise cycle is also equipped with soundproofing material.

Figure 3:
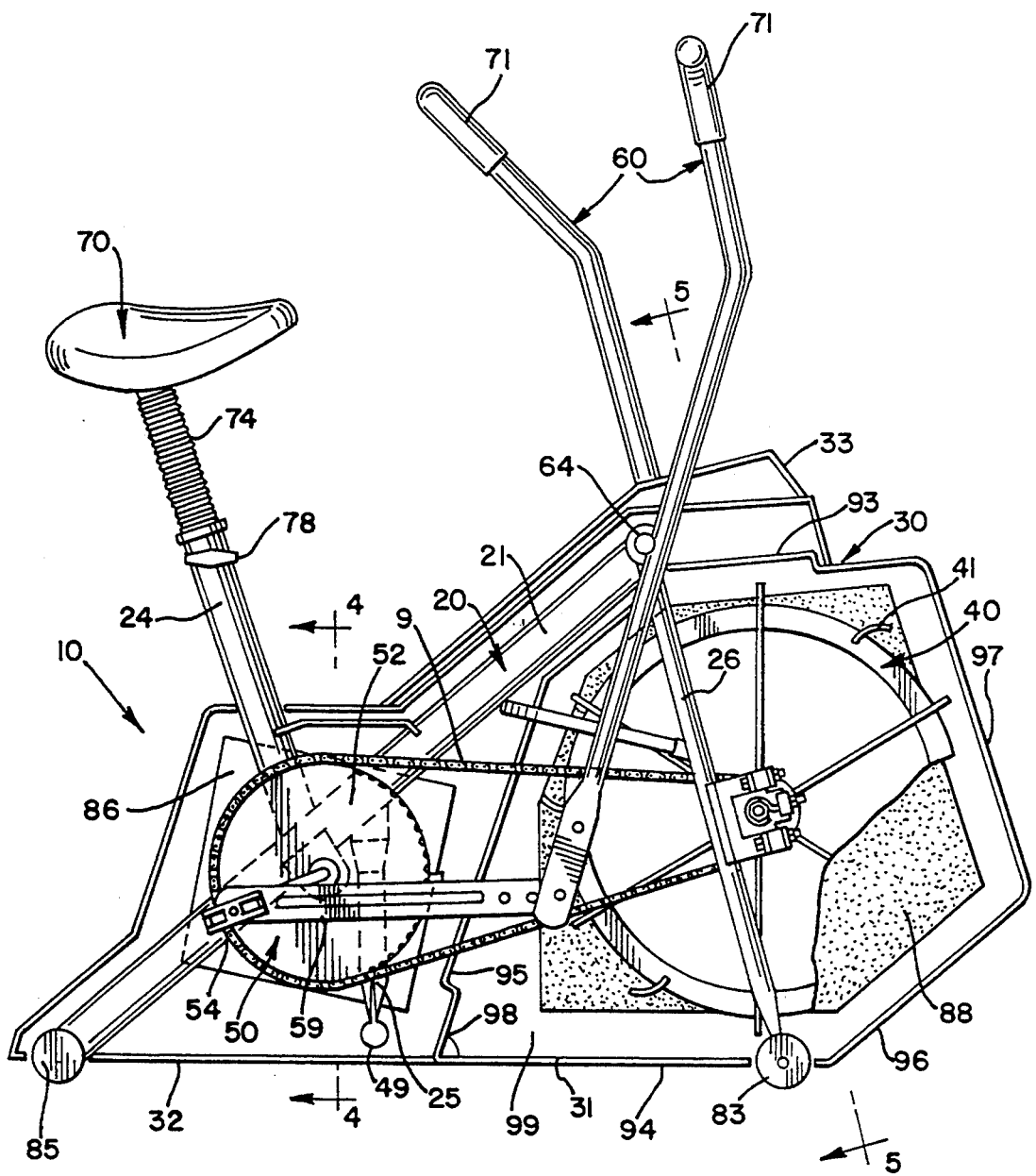
FIG. 3 is a side view of the exercise cycle of FIG. 1 with one side of the housing removed.
Figure 6:
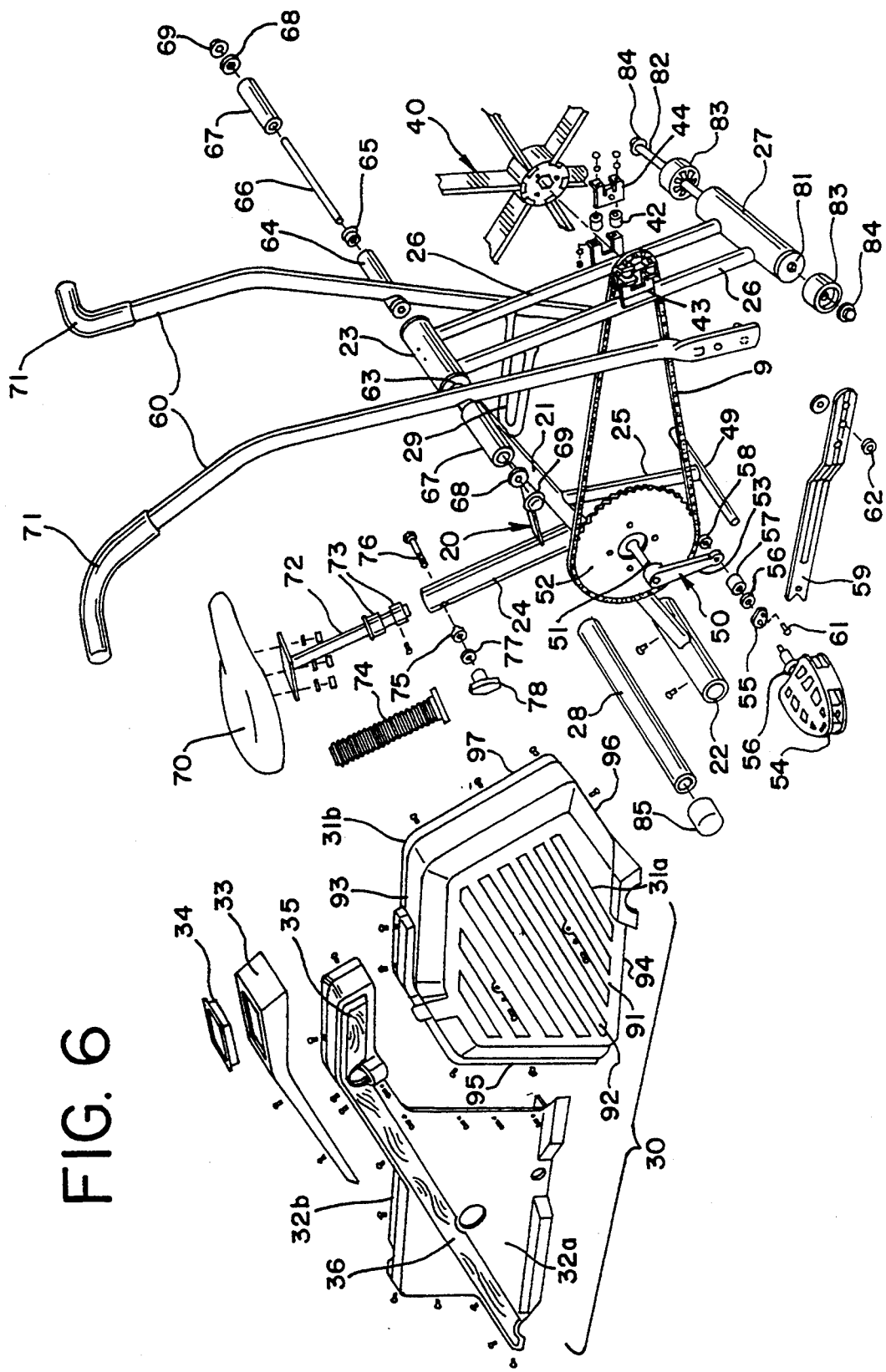
FIG. 6 is an exploded view of the exercise cycle of FIG. 1.

The frame 20 is preferably made of several welded pieces of tubing. As seen in FIGS. 3 and 6, a diagonal frame member 21 extends from rear frame member 22 to a top frame member 23 and supports a seat mast 24 and a central frame member 25. Two tubes 26, which act as forks for the wheel 40, extend from top member 23 to front member 27. A "U" shaped brace 29 fits between diagonal member 21 and tubes 26. A cross member 28 fits through rear member 22 and has foot pads 85 on each end. The front member 27 is fitted with bushings 81 that support an axle 82. Rollers 83 are secured on each end of axle 82 by push nuts 84.

The housing 30 is attached to the frame 20 and is preferably made from molded plastic and comprises two compartments, a first compartment surrounding the wheel, referred to as a front shroud 31, made from right and left side members 31a and 31b, and a second compartment surrounding the crank, referred to as a rear chain guard 32, made from right and left side members 32a and 32b. A console 33 fits on top of the chain guard 32 and holds a monitor 34 used to display useful information about the exercise workout. Each side of the chain guard 32 preferably supports two pieces of wood trim 35 and 36 to add to the appearance of the exercise cycle 10.

The front shroud 31 has two unique features. First, it comprises solid panels and second, it generally forms a polyhedron. Each side member 31a and 31b has a side wall panel 91 generally perpendicular to the axis of rotation of wheel 40 and several edge panels extending from the side wall panels 91. The side wall panels 91 may preferably include ribs 92 to increase the strength of the side wall panels 91, as well as add to the aesthetic appearance of the exercise cycle 10. The edge panels include a top panel 93, a bottom panel 94, a rear panel 95 and a front panel made of two panel sections 96 and 97 connected at an obtuse angle. The top panel 93 is contoured and slopes downwardly at its rear side. All of the panels 91 and 93-97 are molded as one monolithic piece. The edge panels 93-97 on side member 31a overlap the edge panels 93-97 on side member 31b so that the two side members can be fastened together to form a compartment. The solid, unvented, nature of the panels 91 and 93-97 enclose the wheel 40 and limit, and preferably prevent or nearly prevent, air from outside the housing 30 from contacting the wheel 40.

The side wall panels 91 and edge panels 93-97 generally define a polyhedron. The polyhedron includes an internal shape (FIG. 3) that provides dead space within the housing such that air moved by rotation of the wheel eddies inside of the housing. The bottom panel 94 and rear panel 95 form an angle 98 of less than 90°, preferably between about 80° and 60°, and most preferably about 70°. This provides a fairly large area 99 in which air can eddie.

Air resistance wheel 40 comprises air resistance blades or vanes 41. The wheel 40 is supported by frame 20 between tubes 26. As best seen in FIG. 8, the wheel 41 is mounted using rubber mounts 42 to prevent vibrations of the wheel 40 and its driving chain 9 from being transferred to the frame 20.

Two metal plates 43 are welded to the tubes 26. Two additional metal plates 44 support the wheel 40. The rubber mounts 42 fit between flanges on the metal plates 43 and 44. Two studs extend out of each side of each rubber mount 42, but do not contact each other inside the mount. The studs are used with lock washers and hex nuts to hold the plates 43 and 44 together. Plate 44 has a slotted hole (not shown) to allow for adjustment of the chain tension. An eye bolt 45 around each end of the axle 46 can be tightened by hex nut 47 bearing against tension bracket 48 mounted on the edge of plate 44.

As best seen in FIG. 7, the hub 11 of wheel 40 is equipped with flange bearings 49 through which the axle 46 passes. The flange bearings 49 fit up against a step 13 on the inside of both ends of the hub 11. A metal plate 12 with a hex shaped hole in its center is attached to one side of the wheel hub 11. A drive gear 13 is mounted on the opposite side of the hub 11. The drive gear 13 includes a speed pick up to generate a signal carried by wire 14 to monitor 34, which then displays the speed at which wheel 40 is rotating. The drive gear 13, speed pickup and monitor 34 are well known in the art.

Concentric with hub 11 is a wall 15. Spokes 16 radiate from the hub 11 and intersect wall 15. Drive gear 13 has an arm which engages the spokes between hub 11 and wall 15. A sprocket 17 has a hex extension that fits into metal plate 12. A jam nut 18 holds the sprocket 17 into the plate 12. The outside of metal plate 12 is notched to mate with notches in wall 15. Thus the chain 9 engages sprocket 17 and drives plate 12 and wheel 40. Flat and star washers, spacers and nuts are used to hold the drive gear 13 in place and to mount the wheel 40 on plate 44.

In the preferred embodiment, a three piece crank assembly 50 is used, as best seen in FIG. 4. The crank assembly 50 includes a central shaft 51 with a sprocket 52 attached thereto. A crank arm 53 is secured on each end of the shaft 51, preferably with a cotter bolt that passes through the head of the crank arm 53 and a hole on the end of the shaft 51. The shaft 51 is held by flanged bearings as is common in the art so that the crank 50 is rotatably mounted to the frame 20. Each pedal 54 screws into a threaded hole in the end of a crank arm 53. A bearing 55, two washers 56 and a spacer 57 fit between the pedal 54 and the crank arm 53, and a nut 58 is used to secure the end of the pedal 54 on the opposite side of the crank arm 53. Preferably the pedal 54 includes an insert on which the bearing 55 rides.

The bearing 55 is used to attach a cam arm 59 to the pedal 54. (See FIGS. 1, 2 and 6.) The bearing 55 has two extended ears that fit over the end of cam arm 59. A pin 61 is fit through holes through the ears and cam arm 59 to hold the two pieces together. The cam arm 59 is fastened on its opposite end, via one of three holes, to one of two holes in the bottom end of handlebar 60. The holes allow the user to select an appropriate handlebar position comfortable for the user's arm length. A slide bearing 62 is placed in the desired hole in cam arm 59. A pin (not shown) fits through the bottom of handlebar 60 and through the slide bearing 62 to secure the cam arm 59 to the handlebar 60.

Figure 2:
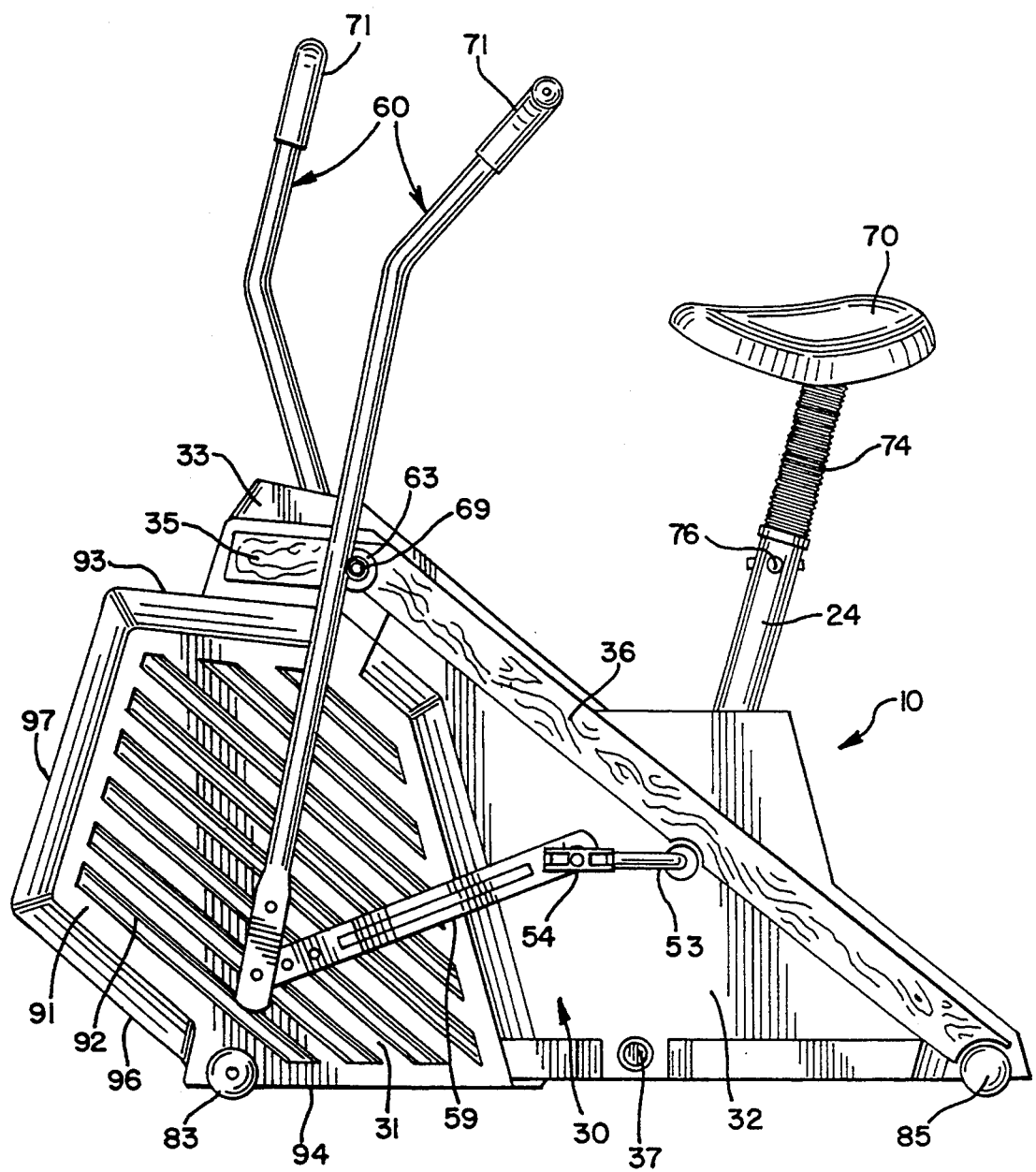
FIG. 2 is a side elevational view of the exercise cycle of FIG. 1.

The handlebar 60 is pivotally connected to the frame 20 at top member 23, which contains pivot bushings 63. Each handlebar 60 has a pivot tube 64 welded on the side. A brass flange bearing 65 fits inside the outer end of each pivot tube 64. A pivot rod 66 extends through both pivot tubes 64 and top member 23. A foot grip 67 is next placed over each pivot tube. A spacer washer 68 and push nut 69 are placed on each end of pivot rod 66 to secure the assembly together. Hand grips 71 are placed over the top ends of each handlebar 60, which are turned outward as shown. If a user desires the handlebars to remain motionless while pedalling, the cam arm 59 on each side may be removed from bearing 55 by removing pin 61. A similar bearing 37 is provided on the ends of tube 49, which is welded cross-wise to the bottom of central frame member 25 as shown in FIG. 6. The ends of tube 49 extend out through the chain guard 32 (FIGS. 1 and 2). Each cam arm 59 may then be pinned to the bearing 37 on opposite sides of the exercise cycle 10.

The seat 70 is fastened to a plate welded to the end of seat post 72 (FIG. 6). Two bushings 73 are placed in set mast 24 to hold seat post 72. A bellows 74 is placed around the portion of seat post 72 extending out of seat mast 24. The seat height is adjustable by the use of a bushing 75 that fits through a hole in one side of seat mast 24. A bolt 76 with a convex head extends through the seat mast 24 on the other side, through bushing 75 and washer 77. A wing nut handle 78 threaded on the end of bolt 76 tightens down on bushing 75, which then clamps against seat post 72 inside of seat mast 24.

The soundproofing material supported by the frame comprises four main components, two on each side of the exercise cycle, and several smaller items. Sound dampening sheets 86 are placed on the inside surface of both sides of the chain guard housing 32a and 32b, as seen in FIGS. 3 and 4. Each sound dampening sheet 86 is generally square with a hole through the center for the crank assembly 50. As shown in FIGS. 3 and 5, another soundproofing member is applied to the inside surface of each of the front compartment side panels 31a and 31b. This member includes a sound dampening sheet 87 and a sheet of foam 88, both cut to fit the corners of the shape of side panels 91. The sound dampening sheets 86 and 87 are secured to the respective housing pieces by adhesive. The foam 88 is also secured to the sound dampening sheet 87 by adhesive.

Another piece of sound dampening sheet 89 is used on the plate 12 opposite the wheel hub 11, as shown in FIG. 7. Again the sound dampening sheet 89 is secured by adhesive to plate 12. The final element of soundproofing in the first embodiment of the invention comprises eleven cylindrical shaped foam plugs 79. The plugs 79 are sized to fit inside the wheel 40 between the hub 11 and wall 15, separated by spokes 16. The plugs 79 contact each of these surfaces. Six plugs 79 are used on the side of wheel 40 to which the sprocket 17 attaches. Only five plugs 79 are used on the opposite side, as one of the spaces between spokes 16 is occupied by the arm extending from drive gear 13 for the speed pick up.

Figure 9:
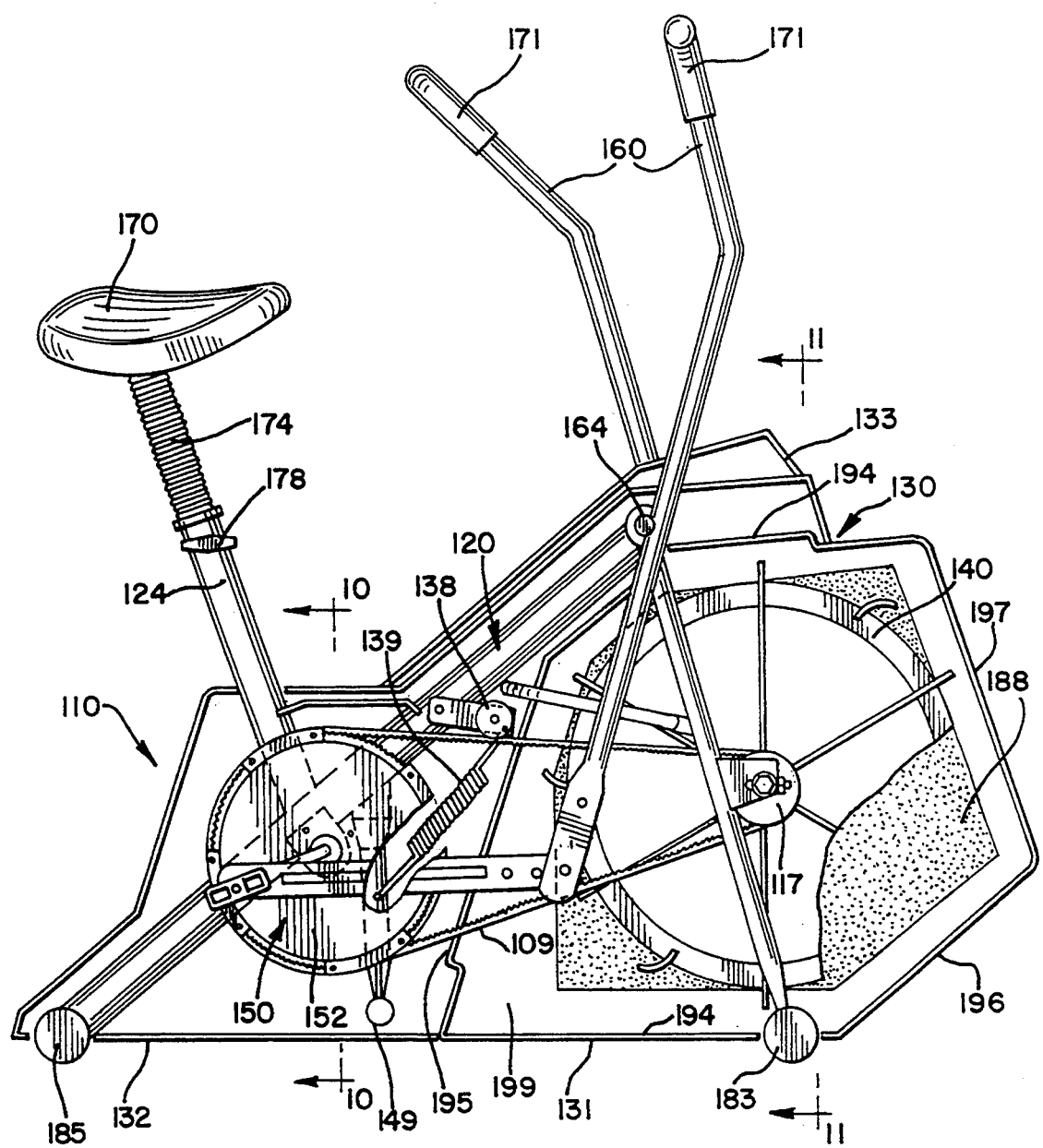
FIG. 9 is a side view like FIG. 3 of a second embodiment of the invention.

A second embodiment of the invention is shown in FIGS. 9–11. This embodiment is identical in most respects to the first embodiment. Therefore, the same reference numbers, with an addend of 100, have been used on the FIGS. For example, housing members 131 and 132 of exercise cycle 110 are identical to housing members 31 and 32 of exercise cycle 10. The major difference is that the second embodiment uses a belt 109 instead of a chain 9. The belt 109 is tensioned by a pivotally mounted pulley 138 tensioned by a spring 139 (FIG. 9). Of course a pulley 152 is used on crank assembly 150 instead of a sprocket 52, and a pulley 117 is used on the wheel 140 instead of a sprocket 17. One other difference is that the belt drive is inherently quieter than the chain drive. As a result, the exercise cycle 110 does not include a dampening sheet on the chain guard 132 or front shroud 131. The foam 188 is adhered directly to the side wall panels 131 (FIG. 11). No foam plugs 79 or dampening sheet 89 are required either. It may be possible to mount the wheel 140 directly on the frame 120 without the need for rubber mounts 42.

A preferred material for use as the sound dampening sheets 86, 87 and 89 is 0.045 inch thick GP-3 Damping Sheet from Soundcoat Company Inc., 1 Burt Drive, Deer Park, N.Y. 11729, preferably secured by an acrylic adhesive such as Soundcoat's MD-K pressure sensitive adhesive. This dampening sheet is a filled vinyl copolymer, and has a weight of 0.4 lb/ft². The adhesive, at a layer of 0.005 inches, provides a 180° peel strength of 6–7 lb/in. initially, and 10–12 lb/in. after 30 days. The foam 88 is preferably an open cell foam. A preferred foam is polyurethane polyester foam. The foam with the dampening sheet already attached is available as ¾" Foam Damping Sheet from Soundcoat.

The foam plugs 79 are preferably a closed cell foam, such as Soundcoat's CSRM closed cell foam, which has a compression deflection of 5–9 psi and a density of 9–14 lb/ft³. The plugs may be coated with Soundcoat's MD-k pressure sensitive adhesive on one end to keep them adhered to the inside of the wheel 40.

Since the air is limited from entering housing 30, it may be necessary to use a faster wheel speed than with other air resistance exercise cycles to obtain satisfactory resistance. This may be accomplished by using a smaller front-to-rear sprocket (or pulley) ratio than is typical. In the preferred embodiment, the front wheel 40 rotates about 10.5 times for each revolution of the crank 50.

It has been found that many belts are not suitable for driving the wheel. The preferred belt is a poly "V" belt with a Kevlar tensile member, such as from Pirelli Power Transmission Corporation.

With either of these embodiments, it is believed that at the user's ear level, the exercise cycle will produce a noise level of less than 60 decibels when pedalled at 50 rpm. Since the decibel scale is a logarithmic function, a decrease of 5–10 decibels from the level of a typical air resistance exercise cycles is a considerable improvement.

The main function of plugs 79 is to reduce the pitch of the sound emanating from wheel 40. It may also be possible to use a clay material in the cavities next to the hub 11 of wheel 40, or a curable liquid sound dampening material.

The need for dampening sheets 86 and 87 is partly a function of the type of drive (chain or belt), but is also partly a function of the rigidity of the housing members. It is interesting to note that the wood trim 36 affects this rigidity. The preferred housing members are molded of polystyrene.

While the preferred embodiments of the invention are air resistance exercise cycles, it will be appreciated that many of the novel features of the invention will be applicable to other exercise devices, particularly other exercise cycles.

It should be appreciated that the apparatus of the present invention is capable of being incorporated in the form of a variety of embodiments, only a few of which have been illustrated and described above. The invention may be embodied in other forms without departing from its spirit or essential characteristics. For example, it may be possible to connect the pedals directly to the wheel, eliminating the chain or belt drive. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:
1. An air resistance exercise cycle comprising:
   a) a frame;
   b) pedals attached to a crank rotatably mounted to said frame;
   c) a wheel comprising air resistance blades rotatably supported by said frame and connected to said crank so as to be driven by rotation of said crank; and d) a housing, comprising solid panels, surrounding and enclosing said wheel so as to generally prevent air from outside the housing from contacting the wheel, said housing having an internal shape that provides dead space within the housing such that the air moved by rotation of the wheel eddies inside of said housing.

2. The exercise cycle of claim 1 further comprising soundproofing material supported by said frame to absorb sound generated by operation of the exercise cycle when said crank is rotated.

3. The exercise cycle of claim 2 wherein the soundproofing material absorbs sound produced by rotation of said wheel.

4. The exercise bicycle of claim 1 wherein the soundproofing material comprises a foam material.

5. The exercise device of claim 2 wherein the foam is an open cell foam.

6. The exercise cycle of claim 2 wherein the foam comprises sponge rubber.

7. The exercise cycle of claim 1 wherein the soundproofing material is mounted to said housing.

8. The exercise cycle of claim 1 wherein the housing comprises two compartments, a first compartment surrounding the wheel and a second compartment surrounding the crank.

9. The exercise cycle of claim 1 wherein the wheel comprises a pitch reduction material that lowers the pitch of sound emanating from the wheel when it is rotated.

10. The exercise cycle of claim 9 wherein the pitch reduction material comprises clay.

11. The exercise cycle of claim 1 wherein the housing comprises two side wall panels generally perpendicular to the axis of rotation of the wheel and edge panels extending between the side wall panels, the side wall and edge panels generally defining a polyhedron.

12. The exercise cycle of claim 11 wherein the edge panels comprise a top panel, a bottom panel, a rear panel and a front panel made of two panel sections connected at an obtuse angle.

13. The exercise cycle of claim 12 wherein the bottom panel and the rear panel form an angle of between about 80° and 60°.

14. The exercise cycle of claim 1 wherein the crank is connected to the wheel by pulleys and a belt.

15. The exercise cycle of claim 1 further comprising: soundproofing material such that when the cycle is pedaled at 50 rpm, the sound emanating from the cycle is less than 60 decibels at the ear level of the user.

* * * * *